United States Patent
Kisilev et al.

(10) Patent No.: US 10,140,709 B2
(45) Date of Patent: Nov. 27, 2018

(54) AUTOMATIC DETECTION AND SEMANTIC DESCRIPTION OF LESIONS USING A CONVOLUTIONAL NEURAL NETWORK

(71) Applicant: International Business Machines Corporation, Armonk, NY (US)

(72) Inventors: Pavel Kisilev, Maalot (IL); Eliyahu Sason, Kiryat Ata (IL)

(73) Assignee: International Business Machines Corporation, Armonk, NY (US)

( * ) Notice: Subject to any disclaimer, the term of this patent is extended or adjusted under 35 U.S.C. 154(b) by 84 days.

(21) Appl. No.: 15/442,718

(22) Filed: Feb. 27, 2017

(65) Prior Publication Data
US 2018/0247405 A1    Aug. 30, 2018

(51) Int. Cl.
G06T 7/00      (2017.01)
G06K 9/66      (2006.01)
G06K 9/62      (2006.01)
G06K 9/46      (2006.01)
G06T 3/40      (2006.01)
(Continued)

(52) U.S. Cl.
CPC .......... *G06T 7/0012* (2013.01); *A61B 5/7267* (2013.01); *A61B 5/7275* (2013.01); *G06K 9/4604* (2013.01); *G06K 9/4671* (2013.01); *G06K 9/52* (2013.01); *G06K 9/6256* (2013.01); *G06K 9/6267* (2013.01); *G06K 9/66* (2013.01); *G06T 3/40* (2013.01); *G06K 2009/4666* (2013.01); *G06K 2209/05* (2013.01); *G06T 2207/30096* (2013.01)

(58) Field of Classification Search
None
See application file for complete search history.

(56) References Cited

U.S. PATENT DOCUMENTS 8,879,813 B1 * 11/2014 Solanki ................. G06T 7/0014
382/128
2003/0194124 A1 * 10/2003 Suzuki ................. G06T 7/0012
382/156
(Continued)

FOREIGN PATENT DOCUMENTS

EP          2998933          3/2016

OTHER PUBLICATIONS

Kai-Lung Hua et al., "Computer-aided classification of lung nodules on computed tomography images via deep learning technique", Dove Press Journal, Aug. 4, 2015, pp. 2015-2022.
(Continued)

*Primary Examiner* — Shervin Nakhjavan

(57) ABSTRACT

An example system includes a processor to train a convolutional neural network (CNN) to detect features, and train fully connected layers of the CNN to map detected features to semantic descriptors, based on a data set including one or more lesions. The processor is to also receive a medical image to be analyzed for lesions. The processor is to further extract feature maps from the medical image using the trained CNN. The processor is also to detect a region of interest via the trained CNN and generate a bounding box around the detected region of interest. The processor is to reduce a dimension of the region of interest based on the feature maps. The processor is to generate a semantic description of the region of interest via the trained fully connected layers.

20 Claims, 7 Drawing Sheets

(51) Int. Cl.
  *G06K 9/52*  (2006.01)
  *A61B 5/00*  (2006.01)

(56) References Cited

U.S. PATENT DOCUMENTS

| | | | |
|---|---|---|---|
| 2012/0027275 A1* | 2/2012 | Fleming | G06F 19/321 |
| | | | 382/128 |
| 2015/0110372 A1 | 4/2015 | Solanki et al. | |
| 2015/0230773 A1 | 8/2015 | Cho et al. | |
| 2015/0265251 A1* | 9/2015 | Cho | A61B 8/0825 |
| | | | 600/437 |
| 2015/0332111 A1 | 11/2015 | Kisilev et al. | |
| 2016/0019320 A1* | 1/2016 | Kim | G06F 19/00 |
| | | | 703/1 |
| 2016/0048737 A1* | 2/2016 | Kam | G06T 7/0012 |
| | | | 382/131 |
| 2017/0169567 A1* | 6/2017 | Chefd'hotel | G06K 9/00127 |
| 2018/0018553 A1* | 1/2018 | Bach | G06F 17/2765 |
| 2018/0053300 A1* | 2/2018 | Podilchuk | G06T 7/0016 |

OTHER PUBLICATIONS

Angel Cruz-Roa et al., "Automatic detection of invasive ductal carcinoma in whole slide images with convolutional neural networks", SPIE proceedings, vol. 9041, Mar. 20, 2014. can be found at: http://spie.org/Publications/Proceedings/Paper/10.1117/12.2043872.

* cited by examiner

AUTOMATIC DETECTION AND SEMANTIC DESCRIPTION OF LESIONS USING A CONVOLUTIONAL NEURAL NETWORK

BACKGROUND

The present techniques relate to detecting and describing lesions. More specifically, the techniques relate to automatically detecting and semantically describing lesions using a trained convolutional neural network.

SUMMARY

According to an embodiment described herein, a system can include a processor to train a convolutional neural network (CNN) to detect features, and train fully connected layers of the CNN to map detected features to semantic descriptors, based on a data set including one or more lesions. The processor can also further receive a medical image to be analyzed for lesions. The processor can also extract feature maps including detected features from the medical image using the trained CNN. The processor can detect a region of interest via the trained CNN and generate a bounding box around the detected region of interest. The processor can also reduce a dimension of the region of interest based on the feature maps. The processor can also further generate a semantic description of the region of interest via the trained fully connected layers.

According to another embodiment described herein, a method can include training, via a processor, a convolutional neural network (CNN) to detect features, and training fully connected layers of the CNN to map the detected features to semantic descriptors, based on a data set including one or more lesions. The method can also further include receiving, via the processor, a medical image to be analyzed for lesions. The method can also include extracting, via the processor, feature maps including detected features from medical image using the trained CNN. The method can include detecting, via the processor, a region of interest via the trained CNN and generate a bounding box around the detected region of interest. The method can further include reducing, via the processor, a dimension of the region of interest based on the feature maps. The method can also further include generating, via the processor, a semantic description of the region of interest via the trained fully connected layers.

According to another embodiment described herein, a computer program product for detecting and describing lesions automatically can include computer-readable storage medium having program code embodied therewith. The computer readable storage medium is not a transitory signal per se. The program code is executable by a processor to cause the processor to train a convolutional neural network (CNN) to detect features, and train fully connected layers of the CNN, to map detected features to semantic descriptors based on a data set including one or more lesions. The program code can also cause the processor to receive a medical image to be analyzed for lesions. The program code can also cause the processor to extract feature maps from medical image using the trained CNN. The program code can also cause the processor to detect a region of interest via the trained CNN and generate a bounding box around the detected region of interest. The program code can also cause the processor to also further reduce a dimension of the region of interest based on the feature maps. The program code can also cause the processor to also generate a semantic description of the region of interest via the trained fully connected layers. The program code can also cause the processor to also further generate and display a diagnostic image including the medical image, the bounding box, and the semantic description.

DETAILED DESCRIPTION

Figure 1:
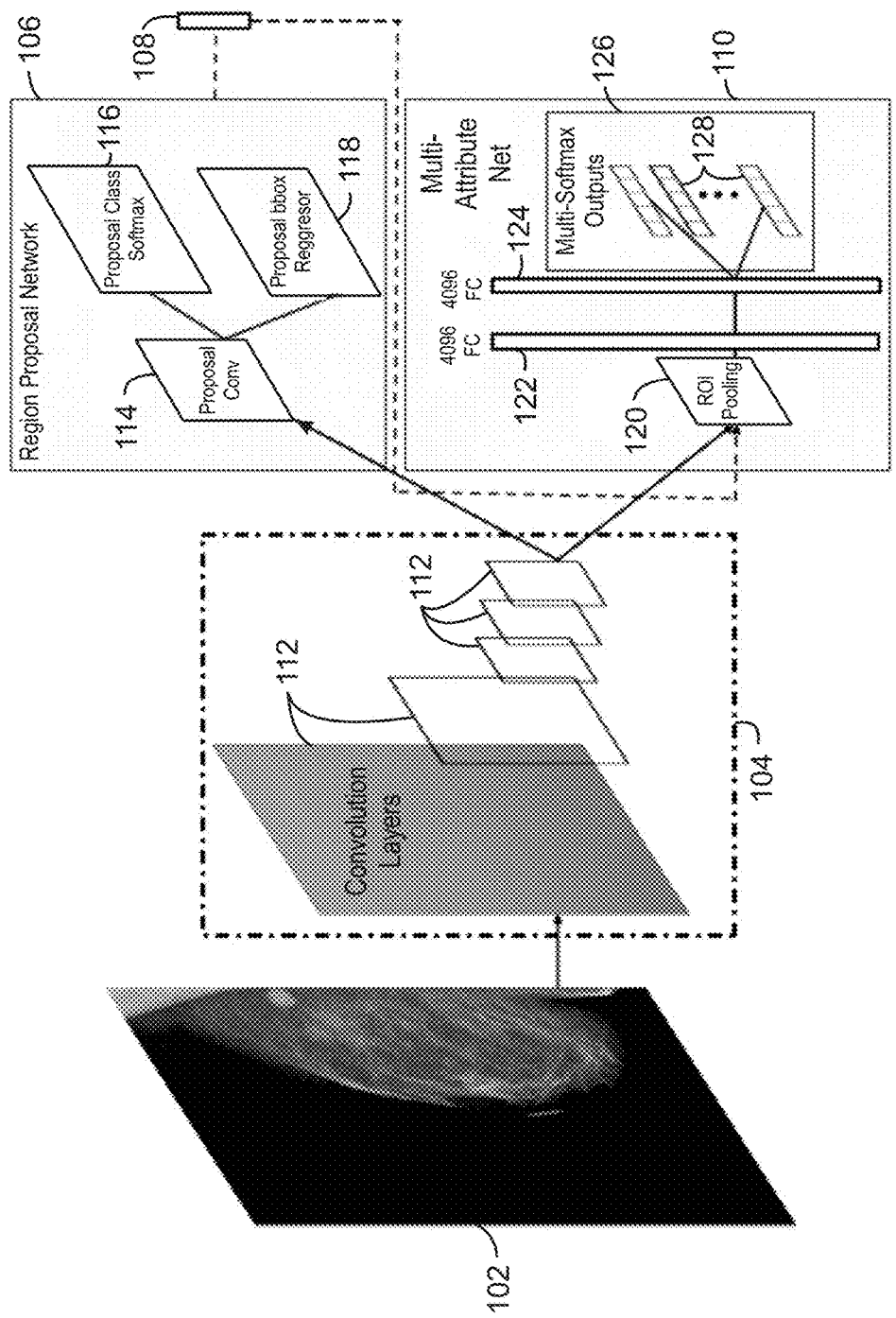
FIG. 1 is a block diagram of an example system that can detect and describe lesions.

Lesions of different organs and modalities may be described by medical professionals in terms of high level semantic descriptors defined in medical standards. A lesion, as used herein, refers to an abnormality or change in tissue of an organism. For example, semantic descriptors of lesions can include shape, boundary type, density, and can include other characteristics that are organ and/or modality specific. In some examples, medical professionals may thus make decisions about the malignancy or benignancy of a lesion based on these characteristics.

Some Computer Aided Detection (CADe) and Diagnosis (CADx) systems use hand-crafted features based on image measurements. Such systems may include the use of histograms of intensity values, shape-related features, texture descriptors, among other features. Using such features, the systems may be able to segment and characterize lesions, and, based on it, make a diagnosis. For example, the diagnosis may be a benign or a malignant tumor.

However, one issue with CADx systems is the lack of intelligibility of the diagnostic decision process. For example, such systems may not have an ability to interpret and describe medical images in semantic terms.

According to implementations of the present techniques a processor may automatically detect and semantically describe one or more lesions in a received image, and generate and display a diagnostic image based on the detected lesions. For example, an example system may include a processor to train a convolutional neural network (CNN) to detect features, and train fully connected layers of the CNN to map detected features to semantic descriptors, based on a data set including one or more lesions. The processor may receive a medical image to be analyzed for lesions. For example, the image may include one or more lesions or be an image of a location that is prone to producing malignant tumors. The processor may also extract feature maps from the medical image using the trained CNN. For example, the feature maps may include one or more detected features. The processor may further detect a region of interest via the trained CNN and generate a bounding box around the detected region of interest. The processor may then reduce a dimension of the region of interest based on the feature maps. The processor may then generate a semantic description of the region of interest via the trained fully connected layers. In some examples, the processor may then generate and display a diagnostic image including the medical image, the bounding box, and the semantic description. Thus, the present techniques may be able to accurately and efficiently identify and semantically describe lesions such as tumors in medical images automatically. The present techniques may be able to identify any number of lesions, such as tumors, present in an image concurrently. Thus, the techniques may enable detecting lesions that may have otherwise been missed. Moreover, the present techniques generate semantic descriptions that are easily understood by medical professionals, such as radiologists. In addition, the present techniques enable areas with higher probability of malignancy to be separated from less probable areas and inspected by a medical professional. Thus, the techniques described herein may improve both the efficiency and the accuracy of diagnosis.

In some scenarios, the techniques described herein may be implemented in a cloud computing environment. As discussed in more detail below in reference to at least FIGS. 4, 5, and 6, a computing device configured to detect and describe lesions automatically may be implemented in a cloud computing environment. It is understood in advance that although this disclosure may include a description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

FIG. 1 is a block diagram of an example system that can detect and describe lesions. The system is generally referred to using the reference number 100 and can be implemented at least in part using the computing device 400 of FIG. 4 below.

The example system 100 includes a medical image 102 to be analyzed by the system 100. For example, the medical image 102 can be received by a first convolutional layer of a CNN 104. The CNN 104 is communicatively connected to a region proposal network 106. For example, the region proposal network 106 may be another CNN. The region proposal network 106 can output a region of interest 108 to a multi-attribute net 110 that is communicatively coupled to both the region proposal network 106 and the CNN 104. The CNN includes a number of convolutional layers 112 for processing received images 102. The region proposal network includes a proposal convolutional layer 114, a proposal class softmax layer 116, and a proposal bounding box reggresor layer 118. The multi attribute net 110 includes an ROI pooling layer 120, two fully connected layers 122, 124 that output multi-softmax outputs 126. For example, the multi-softmax outputs 126 include a number of regions of interest 128. For example, each region of interest 128 may have a number of descriptors indicated by boxes. The descriptors may be, for example, shape descriptors, mass descriptors, margin descriptors, etc.

In the example system 100, a medical image 102 may be received at a first convolutional layer 112 of the CNN 104. The medical image 102 may be processed by the layers 112 of the CNN 104 to extract one or more feature maps. For example, a feature map may be extracted for each dimension of the input image. In some examples, three features maps may be extracted and represented as three dimensional arrays or three dimensional matrices.

The extracted feature maps may be sent from the CNN 104 to both the region proposal network 106 and the multi-attribute net 110. The region proposal network 106 can be trained to generate region of interest (ROI) candidates. For example, the region proposal network 106 can be trained to predict an ROI bounding box coordinates and a bounding box score. For example, the proposal convolutional layer 114 can map the extracted feature maps to a lower-dimensional feature. The proposal class softmax layer 116 can estimate a probability of the ROI bounding box including a tumor for each proposed ROI candidate. The proposal bounding box (bbox) regressor layer 118 can encode the coordinates of the proposed ROI candidates. In some examples, to accommodate for a variety of lesion sizes depending on datasets, the region proposal network may use up to 9 scales of ROI's. For example, the scale of an ROI may range from 16×16 to 1024×1024 in size. Thus, the output of the region proposal network 108 may be any number of region of interest candidates with associated bounding boxes and bounding box scores.

As shown in FIG. 1, the multi-attribute net 110 may receive the region of interest candidates with bounding boxes from the RPN 106 and corresponding feature map for each region of interest from the CNN 104. In some examples, the ROI pooling layer 120 of the multi-attribute net 110 can sample the feature map to extract an area corresponding to the bounding box for each region of interest. In some examples, the multi-attribute net 110 can be trained to jointly predict multiple labels simultaneously. For example, the labels may be semantic descriptors. In some examples, the detecting may be implemented in a multi-task manner. For example, the multi-attribute net 110 may output multiple layers.

In some examples, the regional proposal network 106 and the multi-attribute net 110 can be concurrently trained using the same data set during training of the CNN 104. For example, during the training of the CNN 104, a batch of positive and negative ROI candidates may be taken from two images that may be randomly chosen from a training set of images. A loss function may be defined as a multi-label loss and calculated for each batch using the equation:

$$L(\{P_{ij}\}) = \frac{1}{N}\Sigma_i \Sigma_j w_j l(p_{ij}, c_{ij}) \qquad \text{Eq. 1}$$

where i is the index of an ROI, N is the normalization constant according to mini-batch size, wj are the weights of the J terms that balance their contributions. In some examples, N may be set to 128. The log loss function for true class $c_{ij}$ can be defined using the equation:

$$l(p_{ij}, c_{ij}) = -\Sigma_{1 \ldots vj} t_{ij, cij} \log \qquad \text{Eq. 2}$$

where $t_{ij}$ is 1 if j-th descriptor of i-th ROI is in class $c_{ij}$, and 0 otherwise, and $p_{ij,cij}$ is the predicted probability that the ROI is in class $c_{ij}$. In some examples, the probability $p_{ij}$ for a sample i and label j can be computed as a softmax over the Vj+1 outputs of the fully connected layers. To account for the negative, or for background ROI candidates, the CNN may include a '0-class' category for each one of the semantic descriptor categories. For example, for the shape descriptor, the possible values may be {oval, round, irregular, 0-class}. In some examples, in order to implement Eq. 1, branches of fully connected layers for each one of the semantic descriptors may be created. During the joint training of the network branches, the architecture imposes dependencies of descriptors.

In some examples, the system 100 may then generate and display a diagnostic image including the medical image, the bounding box, and the semantic description. For example, the diagnostic image may show the medical image with one or more bounding boxes surrounding one or more detected lesions and a semantic description for each of the one or more detected lesions. For example, the generated diagnostic image may appear as the example diagnostic image of FIG. 2 below.

It is to be understood that the block diagram of FIG. 1 is not intended to indicate that the system 100 is to include all of the components shown in FIG. 1. Rather, the system 100 can include fewer or additional components not illustrated in FIG. 1 (e.g., additional CNNs, convolutional layers, regions of interest, descriptors, etc.).

Figure 2:
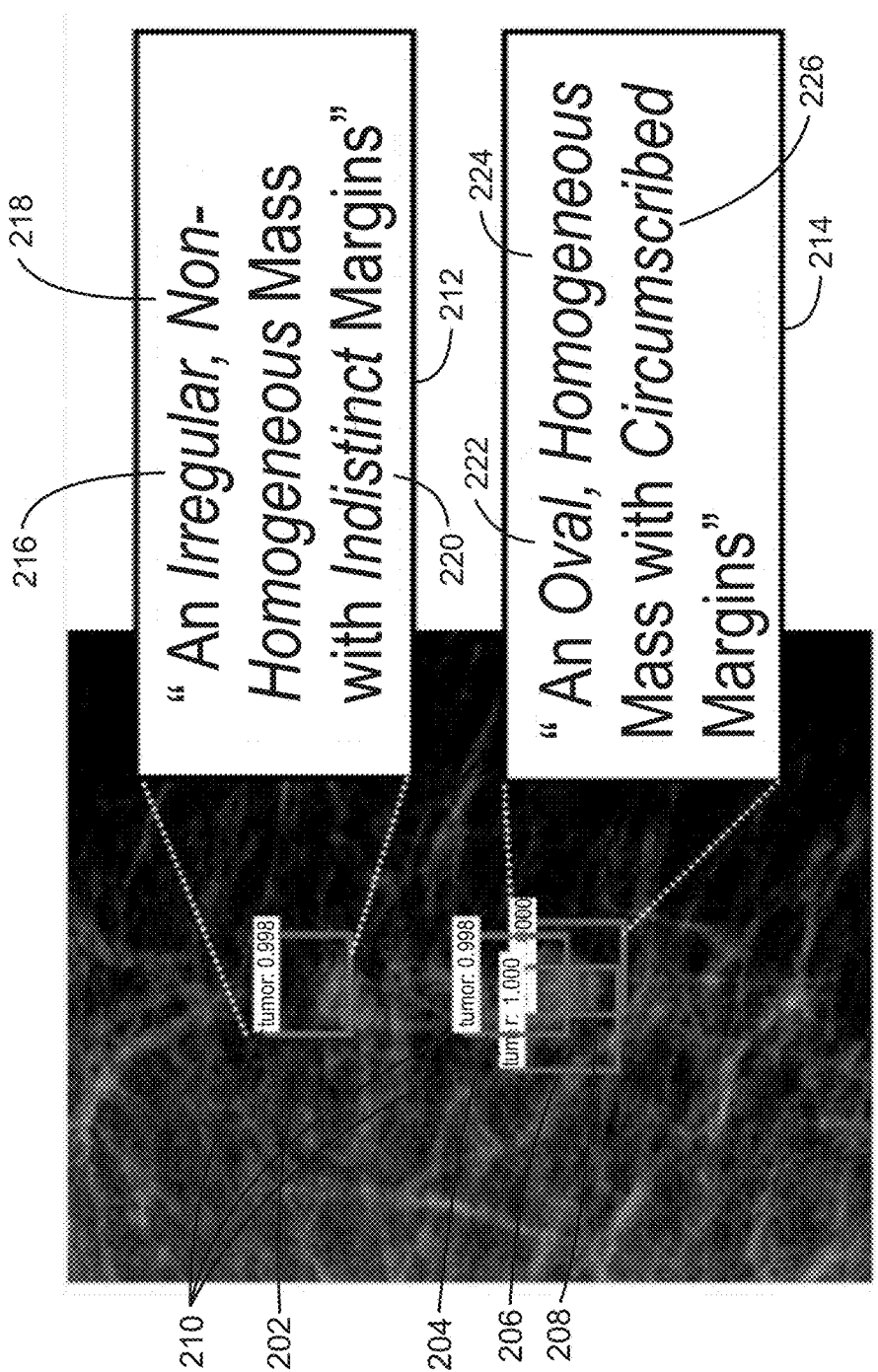
FIG. 2 is an information flow diagram of an example diagnostic image describing detected lesions.

FIG. 2 is an information flow diagram of a diagnostic image describing detected regions of interest. The diagnostic image 200 can be generated using the computing device 400 of FIG. 4 or the system 100 of FIG. 1 above.

As shown in FIG. 2, four higher probability detected regions of interest 202, 204, 206, 208 are shown with respective probabilities 210 of 0.998, 0.998, 1.000, 1.000, respectively. Probabilities closer to 1.000 indicate a higher likelihood that a region of interest includes a tumor. For example, the tumor may be benign or malignant. The diagnostic image 200 further includes an automatically generated textual description of potential tumors within the regions of interest 202, 204, 206, 208. For example, the region of interest 202 is associated with the description "an irregular, non-homogenous mass with indistinct margins" 212. The regions of interest 204, 206, 208 are associated with the description "an oval, homogenous mass with circumscribed margins" 214. The descriptions 212, 214 further contain estimated semantic descriptor values 216, 218, 220, 222 that are embedded into predefined templates. For example, the description "an irregular, non-homogenous mass with indistinct margins" 212 contains a shape descriptor value of "irregular" 216, a density descriptor value of "non-homogenous" 218, and a margin descriptor value of "indistinct" 220. In addition, the description "an oval, homogenous mass with circumscribed margins" 214 includes a shape descriptor value of "oval" 222, a density descriptor value of "homogenous" 224, and a margin descriptor value of "circumscribed" 226.

In some examples, any number of regions of interest may have been identified, probabilities calculated for each identified region of interest, and the regions of interest may have been ranked. Then, four higher regions of interest 202, 204, 206, 208 may have been chosen to be included in the diagnostic image 200 based on their respective probabilities 210. For example, the diagnostic image 200 may have been generated according to the method 300 of FIG. 3 described below.

It is to be understood that the block diagram of FIG. 2 is not intended to indicate that the system 200 is to include all of the components shown in FIG. 2. Rather, the system 200 can include fewer or additional components not illustrated in FIG. 2 (e.g., additional dimensions, regions of interest, descriptors, etc.). The information flow diagram of FIG. 2 is not intended to indicate that the operations of the system 200 are to be executed in any particular order, or that all of the operations of the system 200 are to be included in every case. Additionally, the system 200 may perform any suitable number of additional operations.

Figure 3:
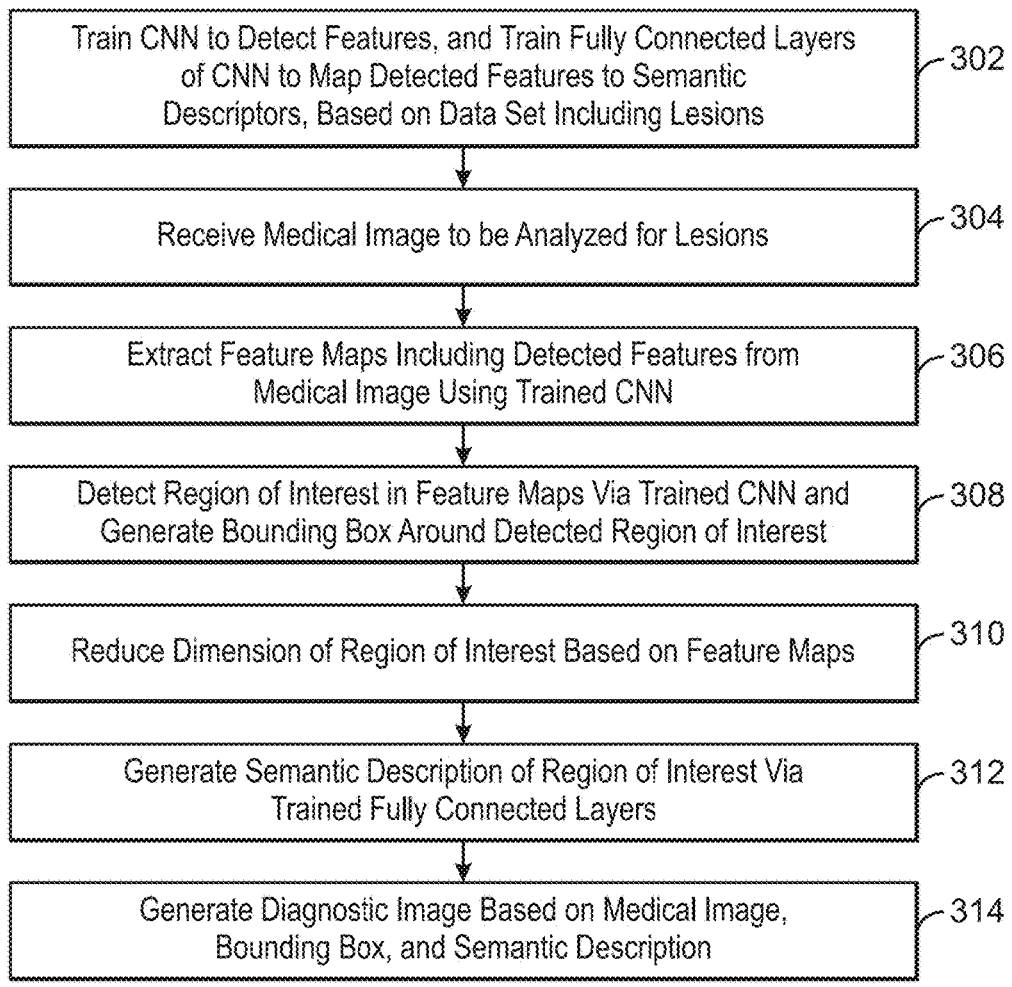
FIG. 3 is a process flow diagram of an example method that can detect and describe lesions.

FIG. 3 is a process flow diagram of an example method that can detect and describe lesions. The method 300 can be implemented with any suitable computing device, such as the computing device 400 of FIG. 4. For example, the method 300 can be implemented via the processor 402 of computing device 400.

At block 302, the processor trains a convolutional neural network (CNN) to detect features, and trains fully connected layers of the CNN to map the detected features to semantic descriptors, based on a data set including one or more lesions. For example, the CNN may receive a data set including positives and negatives. In some examples, training the CNN and training the fully connected layers is performed concurrently using a batch of positive and negative region of interest candidates.

At block 304, the processor receives a medical image to be analyzed for lesions. For example, the medical image may be an image of a body part prone to tumors or suspected of having a tumor.

At block 306, the processor extracts feature maps from the medical image using the trained CNN. For example, the processor can generate a feature map for each dimension of the medical image. For example, the medical image may be any size.

At block 308, the processor detects a region of interest via the trained CNN and generate a bounding box around the detected region of interest. In some examples, the processor can generate a score for the bounding box. For example, the score may indicate the probability that the bounding box includes a tumor.

At block 310, the processor reduces a dimension of the region of interest based on the feature maps. For example, the processor can filter out less probable regions of interest based on calculated probabilities that a plurality of regions of interest are tumors.

At block 312, the processor generates a semantic description of the region of interest via the trained fully connected layers. For example, the processor can generate the semantic description by populating a template description with one or more semantic descriptor values.

At block 314, the processor generates a diagnostic image based on the medical image, the bounding box, and the semantic description. For example, the diagnostic image may include the medical image with one or more bounding boxes including regions of interest and one or more semantic descriptions for each bounding box. In some examples, a group of bounding boxes may be described using a single semantic description. In some examples, the generated diagnostic image may then be displayed for inspection.

The process flow diagram of FIG. 3 is not intended to indicate that the operations of the method 300 are to be executed in any particular order, or that all of the operations of the method 300 are to be included in every case. Additionally, the method 300 can include any suitable number of additional operations.

Figure 4:
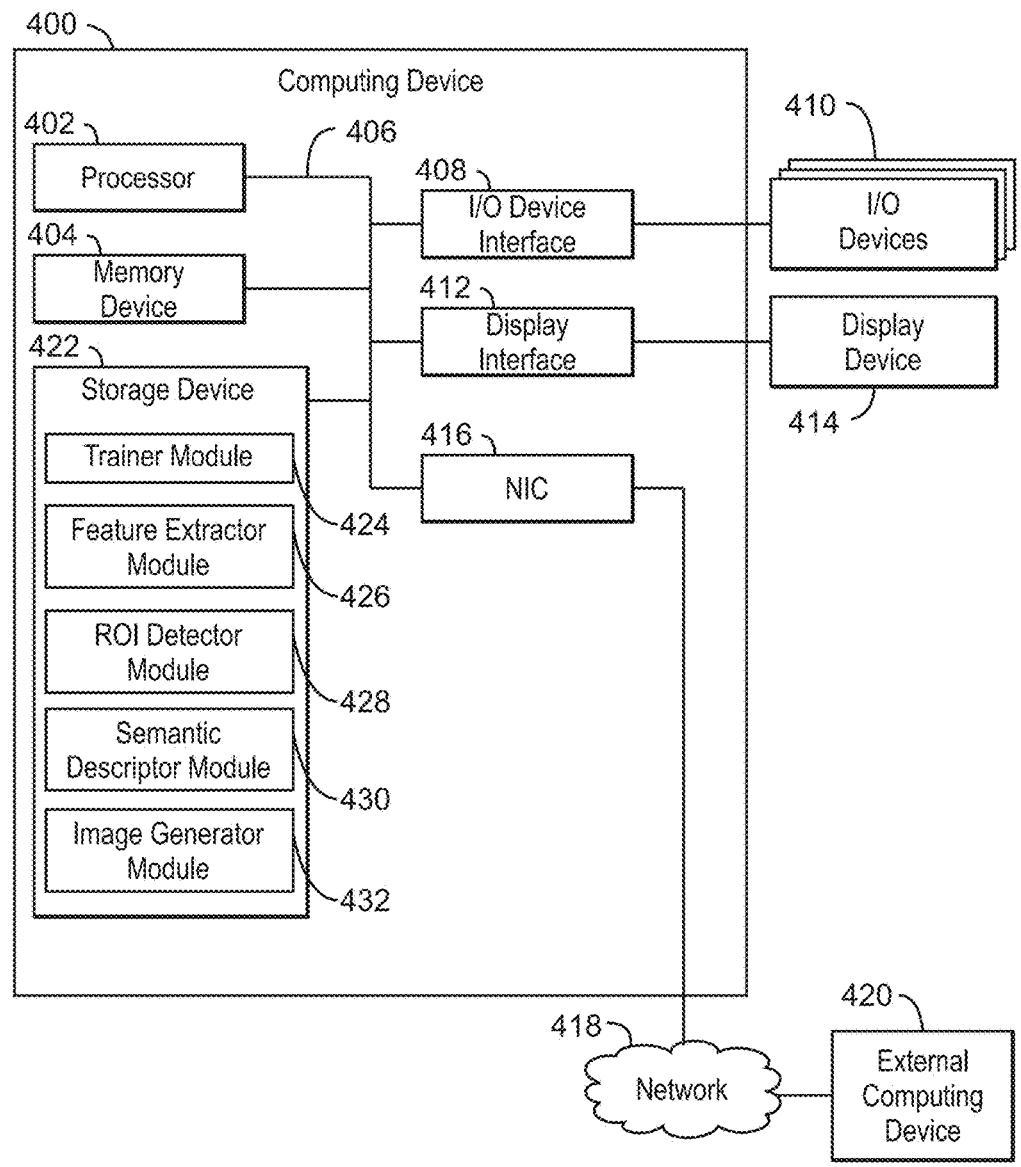
FIG. 4 is a block diagram of an example computing device that can detect and describe lesions.

With reference now to FIG. 4, an example computing device can detect and describe lesions. The computing device 400 may be for example, a server, a network device, desktop computer, laptop computer, tablet computer, or smartphone. In some examples, computing device 400 may be a cloud computing node. Computing device 400 may be described in the general context of computer system executable instructions, such as program modules, being executed by a computer system. Generally, program modules may include routines, programs, objects, components, logic, data structures, and so on that perform particular tasks or implement particular abstract data types. Computing device 400 may be practiced in distributed cloud computing environments where tasks are performed by remote processing devices that are linked through a communications network. In a distributed cloud computing environment, program modules may be located in both local and remote computer system storage media including memory storage devices.

The computing device 400 may include a processor 402 that is to execute stored instructions, a memory device 404 to provide temporary memory space for operations of said instructions during operation. The processor can be a single-core processor, multi-core processor, computing cluster, or any number of other configurations. The memory 404 can include random access memory (RAM), read only memory, flash memory, or any other suitable memory systems.

The processor 402 may be connected through a system interconnect 406 (e.g., PCI®, PCI-Express®, etc.) to an input/output (I/O) device interface 408 adapted to connect the computing device 400 to one or more I/O devices 410. The I/O devices 410 may include, for example, a keyboard and a pointing device, wherein the pointing device may include a touchpad or a touchscreen, among others. The I/O devices 410 may be built-in components of the computing device 400, or may be devices that are externally connected to the computing device 400.

The processor 402 may also be linked through the system interconnect 406 to a display interface 412 adapted to connect the computing device 400 to a display device 414. The display device 414 may include a display screen that is a built-in component of the computing device 400. The display device 414 may also include a computer monitor, television, or projector, among others, that is externally connected to the computing device 400. In addition, a network interface controller (NIC) 416 may be adapted to connect the computing device 400 through the system interconnect 406 to the network 418. In some embodiments, the NIC 416 can transmit data using any suitable interface or protocol, such as the internet small computer system interface, among others. The network 418 may be a cellular network, a radio network, a wide area network (WAN), a local area network (LAN), or the Internet, among others. An external computing device 420 may connect to the computing device 400 through the network 418. In some examples, external computing device 420 may be an external web-server 420. In some examples, external computing device 420 may be a cloud computing node.

The processor 402 may also be linked through the system interconnect 406 to a storage device 422 that can include a hard drive, an optical drive, a USB flash drive, an array of drives, or any combinations thereof. In some examples, the storage device may include a trainer module 424, a feature extractor module 426, an ROI detector module 428, a semantic descriptor module 430, and an image generator module 432. In some examples, one or more of the modules 424-432 may be implemented in a convolutional neural network (CNN). The trainer module 424 can train a convolutional neural network (CNN) to detect features, and train fully connected layers of the CNN to map detected features to semantic descriptors, based on a data set including one or more lesions. The feature extractor module 426 can then receive a medical image to be analyzed for lesions. The feature extractor module 426 can also extract feature maps from the medical image using the trained CNN. For example, the feature maps may include one or more detected features. The ROI detector module 428 can detect a region of interest via the trained CNN and generate a bounding box around the detected region of interest. In some examples, the ROI detector 428 can also calculate a probability that the region of interest is a tumor. In some examples, the ROI detector 428 can rank the bounding box with other bounding boxes of other detected regions of interest based on a calculated probability for each detected region of interest that each region of interest is a tumor. The semantic descriptor module 430 can reduce a dimension of the region of interest based on the feature maps. For example, the semantic descriptor module 430 can filter out less probable regions of interest based on calculated probabilities that a plurality of regions of interest are tumors. The region of interest may include a higher probability than other regions of interest in the plurality of regions of interest. The semantic descriptor module 430 can then generate a semantic description of the region of interest via the trained fully connected layers. For example, the semantic description may include one or more semantic descriptors including a shape, a boundary type, a density, or any combination thereof. In some examples, the image generator module 432 can then generate and display a diagnostic image including the medical image, the bounding box, and the semantic description. For example, the diagnostic image may be generated based on the region of interest with the reduced dimension.

It is to be understood that the block diagram of FIG. 4 is not intended to indicate that the computing device 400 is to include all of the components shown in FIG. 4. Rather, the computing device 400 can include fewer or additional components not illustrated in FIG. 4 (e.g., additional memory components, embedded controllers, modules, additional network interfaces, etc.). Furthermore, any of the functionalities of the trainer module 424, the feature extractor module 426, the ROI detector module 428, the semantic descriptor module 430, and the image generator module 432, may be partially, or entirely, implemented in hardware and/or in the processor 402. For example, the functionality may be implemented with an application specific integrated circuit, logic implemented in an embedded controller, or in logic implemented in the processor 402, among others. In some embodiments, the functionalities of the trainer module 424, the feature extractor module 426, the ROI detector module 428, the semantic descriptor module 430, and the image generator module 432, can be implemented with logic, wherein the logic, as referred to herein, can include any suitable hardware (e.g., a processor, among others), software (e.g., an application, among others), firmware, or any suitable combination of hardware, software, and firmware.

Figure 5:
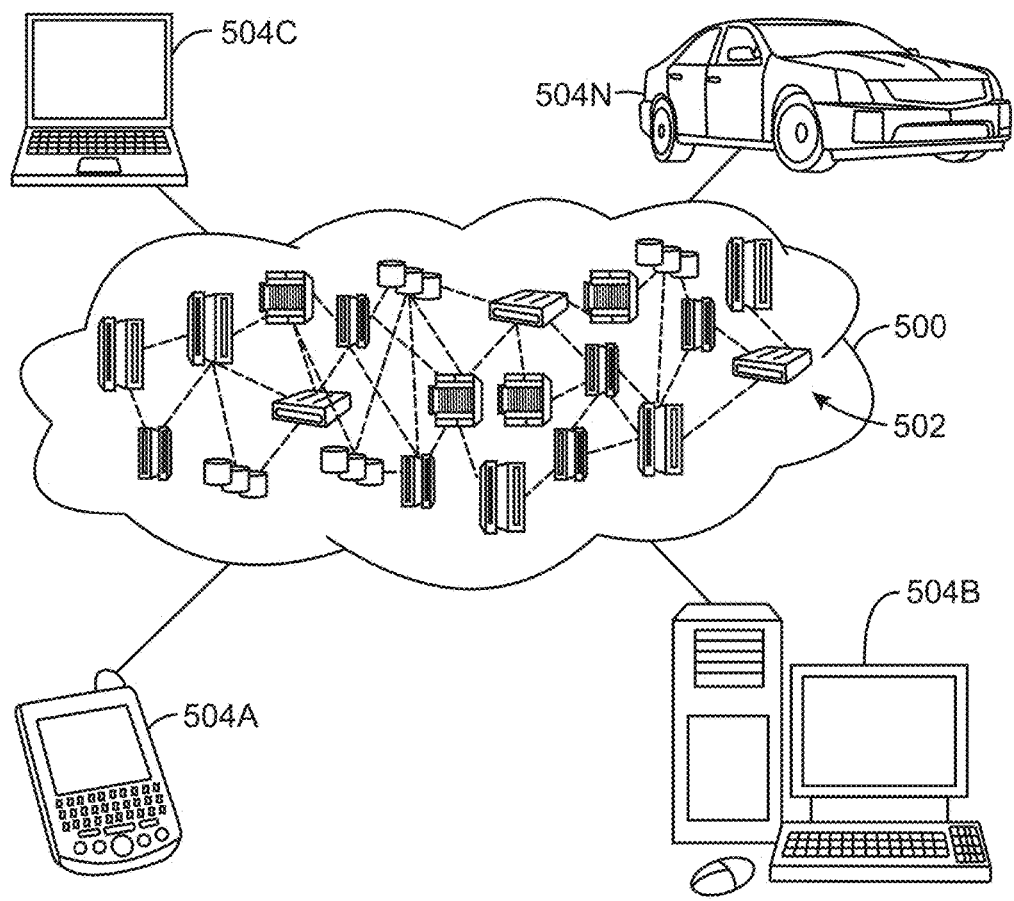
FIG. 5 is a block diagram of an example cloud computing environment according to embodiments described herein.

Referring now to FIG. 5, an illustrative cloud computing environment 500 is depicted. As shown, cloud computing environment 500 comprises one or more cloud computing nodes 502 with which local computing devices used by cloud consumers, such as, for example, personal digital assistant (PDA) or cellular telephone 504A, desktop computer 504B, laptop computer 504C, and/or automobile computer system 504N may communicate. Nodes 502 may communicate with one another. They may be grouped (not shown) physically or virtually, in one or more networks, such as Private, Community, Public, or Hybrid clouds as described hereinabove, or a combination thereof. This allows cloud computing environment 500 to offer infrastructure, platforms and/or software as services for which a cloud consumer does not need to maintain resources on a local computing device. It is understood that the types of computing devices 504A-N shown in FIG. 5 are intended to be illustrative only and that computing nodes 502 and cloud computing environment 500 can communicate with any type of computerized device over any type of network and/or network addressable connection (e.g., using a web browser).

Figure 6:
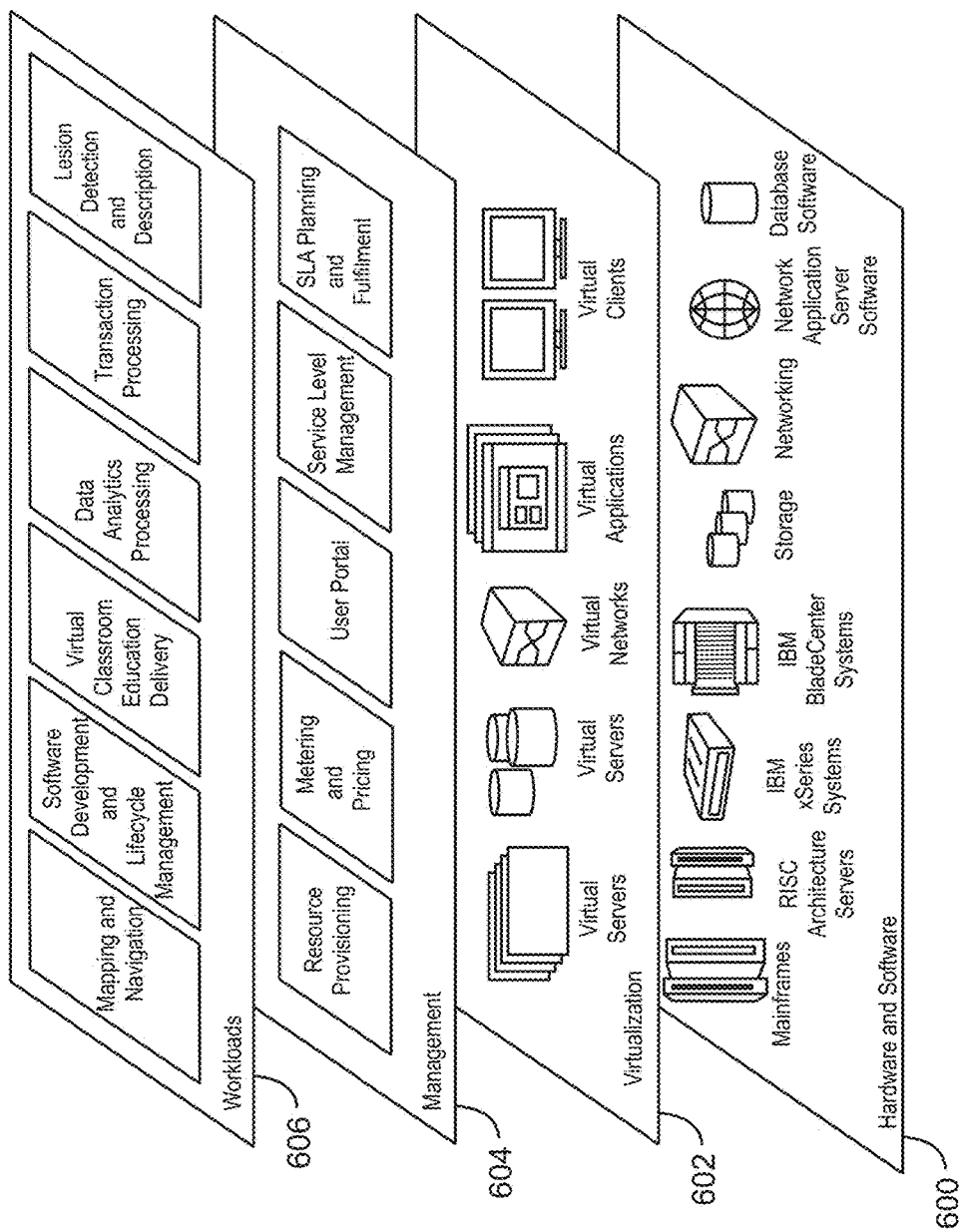
FIG. 6 is an example abstraction model layers according to embodiments described herein.

Referring now to FIG. 6, a set of functional abstraction layers provided by cloud computing environment 500 (FIG. 5) is shown. It should be understood in advance that the components, layers, and functions shown in FIG. 6 are intended to be illustrative only and embodiments of the invention are not limited thereto. As depicted, the following layers and corresponding functions are provided.

Hardware and software layer 600 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 602 provides an abstraction layer from which the following examples of virtual entities may be provided: virtual servers; virtual storage; virtual networks, including virtual private networks; virtual applications and operating systems; and virtual clients. In one example, management layer 604 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide prearrangement for, and procurement of, cloud computing resources for which a future requirement is anticipated in accordance with an SLA.

Workloads layer 606 provides examples of functionality for which the cloud computing environment may be utilized. Examples of workloads and functions which may be provided from this layer include: mapping and navigation; software development and lifecycle management; virtual classroom education delivery; data analytics processing; transaction processing; and lesion detection and description.

The present techniques may be a system, a method or computer program product. The computer program product may include a computer readable storage medium (or media) having computer readable program instructions thereon for causing a processor to carry out aspects of the techniques described herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present techniques may be assembler instructions, instruction-set-architecture (ISA) instructions, machine instructions, machine dependent instructions, microcode, firmware instructions, state-setting data, or either code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present techniques.

Aspects of the present techniques are described herein with reference to flowchart illustrations and/or block diagrams of methods, apparatus (systems), and computer program products according to embodiments of the techniques. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 7:
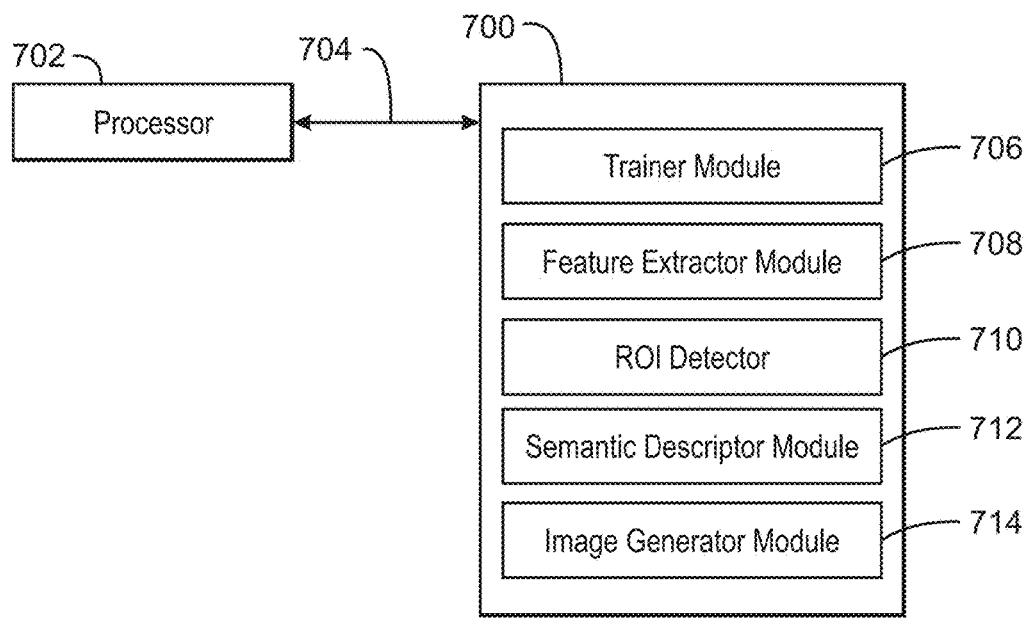
FIG. 7 is an example tangible, non-transitory computer-readable medium that can detect and describe lesions automatically.

Referring now to FIG. 7, a block diagram is depicted of an example tangible, non-transitory computer-readable medium 700 that can detect and describe lesions automatically. The tangible, non-transitory, computer-readable medium 700 may be accessed by a processor 702 over a computer interconnect 704. Furthermore, the tangible, non-transitory, computer-readable medium 700 may include code to direct the processor 702 to perform the operations of the method 300 of FIG. 3 above.

The various software components discussed herein may be stored on the tangible, non-transitory, computer-readable medium 700, as indicated in FIG. 7. For example, a trainer module 706 includes code to train a convolutional neural network (CNN) to detect features, and train fully connected layers of the CNN, to map detected features to semantic descriptors based on a data set including one or more lesions. In some examples, the trainer module 706 may include code to train the CNN and train the fully connected layers concurrently using a batch of positive and negative region of interest candidates. A feature extractor module 708 includes code to receive a medical image to be analyzed for lesions. The feature extractor module 708 also includes code to extract feature maps including detected features from medical image using the trained CNN. For example, the feature extractor module 708 can extract a feature map for each dimension of the medical image. A region of interest (ROI) detector module 710 includes code to detect a region of interest via the trained CNN and generate a bounding box around the detected region of interest. In some examples, the ROI detector 710 can detect any number of regions of interest. In some examples, the ROI detector module 710 may also include code to calculate a probability that the region of interest is a tumor. For example, the ROI detector module 710 can calculate a probability for each region of interest in the plurality of regions of interest. A semantic descriptor module 712 includes code to reduce a dimension of the region of interest based on the feature maps. In some examples, the semantic descriptor module 712 may include code to rank the plurality of regions of interest based on a calculated probability that the regions include a tumor. In some examples, regions with calculated probabilities below a threshold probability may be filtered out. The semantic descriptor module 712 further includes code to generate a semantic description of the region of interest via the trained fully connected layers. An image generator module 714 includes code to generate and display a diagnostic image including the medical image, the bounding box, and the semantic description. In some examples, the image generator module 714 may include code to generate and display the diagnostic image with a predetermined number of regions of interest with a ranking above a threshold value. In some examples, the image generator module 714 may include code to populate a template description with one or more semantic descriptor values. It is to be understood that any number of additional software components not shown in FIG. 7 may be included within the tangible, non-transitory, computer-readable medium 700, depending on the particular application.

The flowchart and block diagrams in the Figures illustrate the architecture, functionality, and operation of possible implementations of systems, methods, and computer program products according to various embodiments of the present techniques. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present techniques have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising a processor to:
   train a convolutional neural network (CNN) to detect features, and train fully connected layers of the CNN to map detected features to semantic descriptors, based on a data set comprising one or more lesions;
   receive a medical image to be analyzed for lesions;
   extract feature maps comprising detected features from the medical image using the trained CNN;
   detect a region of interest via the trained CNN and generate a bounding box around the detected region of interest;
   reduce a dimension of the region of interest based on the feature maps; and
   generate a semantic description of the region of interest via the trained fully connected layers.

2. The system of claim 1, wherein the processor is to calculate a probability that the region of interest comprises a tumor.

3. The system of claim 1, wherein the processor is to filter out less probable regions of interest based on calculated probabilities that a plurality of regions of interest comprise tumors, wherein the region of interest comprises a higher probability than other regions of interests in the plurality of regions of interest.

4. The system of claim 1, wherein the feature maps comprise one or more detected features.

5. The system of claim 1, wherein the processor is to rank the bounding box with other bounding boxes corresponding to other detected regions of interest, wherein the ranking is based on a calculated probability that each detected region of interest comprises a tumor.

6. The system of claim 1, wherein the semantic description comprises one or more semantic descriptors comprising a shape, a boundary type, a density, or any combination thereof.

7. The system of claim 1, wherein the processor is to generate and display a diagnostic image comprising the medical image, the bounding box, and the semantic description.

8. A computer-implemented method, comprising:
   training, via a processor, a convolutional neural network (CNN) to detect features, and training fully connected layers of the CNN to map the detected features to semantic descriptors, based on a data set comprising one or more lesions;
   receiving, via the processor, a medical image to be analyzed for lesions;
   extracting, via the processor, feature maps comprising detected features from medical image using the trained CNN;
   detecting, via the processor, a region of interest via the trained CNN and generate a bounding box around the detected region of interest;
   reducing, via the processor, a dimension of the region of interest based on the feature maps; and
   generating, via the processor, a semantic description of the region of interest via the trained fully connected layers.

9. The computer-implemented method of claim 8, wherein training the CNN and training the fully connected layers is performed concurrently using a batch of positive and negative region of interest candidates.

10. The computer-implemented method of claim 8, comprising generating, via the processor, a diagnostic image based on the medical image, the bounding box, and the semantic description.

11. The computer-implemented method of claim 8, comprising generating, via the processor, a score for the bounding box.

12. The computer-implemented method of claim 8, wherein extracting the feature maps comprises extracting a feature map for each dimension of the medical image.

13. The computer-implemented method of claim 8, wherein reducing the dimension of the region of interest comprises filtering out less probable regions of interest based on calculated probabilities that a plurality of regions of interest comprise lesions.

14. The computer-implemented method of claim 8, wherein generating the semantic description of the region of interest comprises populating a template description with one or more semantic descriptor values.

15. A computer program product for detecting and describing lesions automatically, the computer program product comprising a computer-readable storage medium having program code embodied therewith, wherein the computer readable storage medium is not a transitory signal per se, the program code executable by a processor to cause the processor to:
   train a convolutional neural network (CNN) to detect features, and train fully connected layers of the CNN, to map detected features to semantic descriptors based on a data set comprising one or more lesions;
   receive a medical image to be analyzed for lesions;
   extract feature maps comprising detected features from medical image using the trained CNN;
   detect a region of interest via the trained CNN and generate a bounding box around the detected region of interest;
   reduce a dimension of the region of interest based on the feature maps; and
   generate a semantic description of the region of interest via the trained fully connected layers; and
   generate and display a diagnostic image comprising the medical image, the bounding box, and the semantic description.

16. The computer program product of claim 15, comprising program code executable by the processor to calculate a probability that the region of interest comprises a tumor.

17. The computer program product of claim 15, comprising program code executable by the processor to:
   detect a plurality of regions of interest;
   calculate a probability for each region of interest in the plurality of regions of interest;
   rank the plurality of regions of interest based on calculated probability; and
   generate and display the diagnostic image with a predetermined number of regions of interest with a ranking above a threshold value.

18. The computer program product of claim 15, comprising program code executable by the processor to train the CNN and train the fully connected layers concurrently using a batch of positive and negative region of interest candidates.

19. The computer program product of claim 15, comprising program code executable by the processor to extract a feature map for each dimension of the medical image.

20. The computer program product of claim 15, comprising program code executable by the processor to populate a template description with one or more semantic descriptor values.

* * * * *